(12) United States Patent
Hoag et al.

(10) Patent No.: US 10,070,961 B2
(45) Date of Patent: Sep. 11, 2018

(54) FULLY POROUS PROSTHETIC HIP STEM

(75) Inventors: Stephen H. Hoag, Warsaw, IN (US); Dale A. Degroff, Warsaw, IN (US); Douglas H. Wentz, Winona Lake, IN (US); Leslie N. Gilbertson, Warsaw, IN (US); Roy D. Crowninshield, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 2073 days.

(21) Appl. No.: 11/353,392

(22) Filed: Feb. 14, 2006

(65) Prior Publication Data

US 2006/0276906 A1    Dec. 7, 2006

Related U.S. Application Data

(60) Provisional application No. 60/654,156, filed on Feb. 18, 2005.

(51) Int. Cl.
    *A61F 2/36*   (2006.01)
    *A61F 2/30*   (2006.01)

(52) U.S. Cl.
    CPC ............ *A61F 2/36* (2013.01); *A61F 2/30767* (2013.01); *A61F 2/30907* (2013.01); *A61F 2002/30535* (2013.01); *A61F 2250/0058* (2013.01)

(58) Field of Classification Search
    CPC ..... A61F 2/30767; A61F 2/30907; A61F 2/36
    (Continued)

(56) References Cited

U.S. PATENT DOCUMENTS 3,906,550 A * 9/1975 Rostoker et al. .......... 623/23.55
4,650,489 A   3/1987 Thompson
(Continued)

FOREIGN PATENT DOCUMENTS

CA    2598177 C    10/2014
GB    2216425      10/1989
(Continued)

OTHER PUBLICATIONS

Webpage—Zimmer Epoch® Hip Prosthesis.
(Continued)

*Primary Examiner* — Yashita Sharma
(74) *Attorney, Agent, or Firm* — Schwegman Lundberg & Woessner, P.A.

(57) ABSTRACT

A prosthetic hip stem for use in a prosthetic hip joint. The hip stem generally includes a core having a stem portion and a neck portion, a polymer matrix layer substantially covering the stem portion of the core, and a porous metal layer substantially covering the polymer matrix layer. The polymer matrix layer connects the core and the porous metal layer, and may be injection molded therebetween. The neck portion of the hip stem has a relatively thin or slender profile which allows for an increased degree of articulating movement of the hip stem with respect to the acetabular component of a prosthetic hip joint. The neck portion of the hip stem additionally includes a version indicator element, such as a bump or a protrusion, which may be tactilely felt by a surgeon to aid the surgeon in positioning the hip stem during a minimally invasive total hip arthroplasty procedure, for example, where direct visualization of the hip stem by the surgeon may not be possible. Additionally, the core of the hip stem includes grooves, ridges, flats, dimples or other features to enhance the mechanical interconnection between the core and the polymer matrix layer.

24 Claims, 11 Drawing Sheets

(58) Field of Classification Search
USPC .................. 623/23.58, 23.59, 23.25–23.42
See application file for complete search history.

(56) References Cited

U.S. PATENT DOCUMENTS

| | | | |
|---|---|---|---|
| 4,792,339 A | | 12/1988 | Tepi |
| 4,813,963 A | | 3/1989 | Hori et al. |
| 4,828,566 A | | 5/1989 | Griss |
| 4,895,573 A | | 1/1990 | Koeneman et al. |
| 5,007,931 A | | 4/1991 | Smith |
| 5,176,712 A | * | 1/1993 | Homsy ............... 623/23.36 |
| 5,236,457 A | | 8/1993 | Devanathan |
| 5,387,243 A | * | 2/1995 | Devanathan ............ 128/898 |
| 5,443,512 A | * | 8/1995 | Parr et al. ............ 623/23.51 |
| 5,571,202 A | | 11/1996 | Mathys, Sr. et al. |
| 5,593,451 A | | 1/1997 | Averill |
| 5,702,487 A | | 12/1997 | Averill |
| 5,863,295 A | | 1/1999 | Averill |
| 6,136,035 A | | 10/2000 | Lob et al. |
| 6,190,417 B1 | | 2/2001 | Itoman et al. |
| 6,395,327 B1 | | 5/2002 | Shetty |
| 6,514,288 B2 | | 2/2003 | Meulink et al. |
| 6,576,014 B2 | | 6/2003 | Shetty |
| 6,676,706 B1 | | 1/2004 | Mears et al. |
| 6,685,987 B2 | | 2/2004 | Shetty |
| 6,695,884 B1 | | 2/2004 | Townley |
| 6,994,731 B2 | | 2/2006 | Howie |
| 7,001,672 B2 | | 2/2006 | Justin et al. |
| 7,044,975 B2 | | 5/2006 | Cheal |
| 2007/0219641 A1 | | 9/2007 | Dorr et al. |

FOREIGN PATENT DOCUMENTS

| | | |
|---|---|---|
| WO | WO9416649 | 8/1994 |
| WO | WO9420046 | 9/1994 |
| WO | WO9741809 | 11/1997 |

OTHER PUBLICATIONS

Brochure—Zimmer Epoch® Hip Prosthesis.
Surgical Technique—Zimmer Epoch® Hip Prosthesis.
Brochure—Zimmer VerSys® Hip System, Cemented Hip Prosthesis.
Surgical Technique—Zimmer VerSys® Hip system, Cemented Hip Prosthesis.
Brochure—Zimmer VerSys Hip System, Fiber Metal Taper HP Prosthes, Versatile Total Hip Solutions Using Designs and Enhanced Fixation, 97-7862-01 20MIP, Zimmer, Inc. 1997, 4 pages.
Brochure—Zimmer VerSys HIP System, Cemented Hip Prosthesis, Traditional Design, Innovative Features, 97-7853-01 16MIL, Zimmer, Inc. 1999, 4 pages.
Brochure—Zimmer VerSys HIP System, LD/Fx HIP Prostheses, Versatile Solutions for Total and Partial Hip Replacement, 97-7831-01 Rev. 1, 15MM, Zimmer, Inc. 1998, 4 pages.
Page, John "Included Angle" 2007. The Math Open Reference Project. http://www.mathopenref.com/angleincluded.html.
The IPRP dated Aug. 21, 2007 in related International Application No. PCT/US2006/005089.
The International Search Report published Aug. 31, 2006 in related International Application No. PCT/US2006/005089.
Restriction Requirement dated Jul. 30, 2008 in U.S. Appl. No. 11/687,862.
Election filed Aug. 7, 2008 in U.S. Appl. No. 11/687,862.
Office Action dated Aug. 22, 2008 in U.S. Appl. No. 11/687,862.
Amendment filed Dec. 12, 2008 in U.S. Appl. No. 11/687,862.
Restriction Requirement dated Mar. 12, 2009 in U.S. Appl. No. 11/687,862.
Election filed Apr. 6, 2009 in U.S. Appl. No. 11/687,862.
Office Action dated Apr. 17, 2009 in U.S. Appl. No. 11/687,862.
Amendment filed Jul. 24, 2009 in U.S. Appl. No. 11/687,862.
"Canadian Application Serial No. 2,598,177, Office Action dated Apr. 8, 2013", 2 pgs.
"Canadian Application Serial No. 2,598,177, Office Action dated Mar. 22, 2012", 2 pgs.
"Canadian Application Serial No. 2,598,177, Response filed 9-20-12 to Office Action dated Mar. 22, 2012", 41 pgs.
"European Application Serial No. 06734971.2, Office Action dated Mar. 26, 2012", 1 pg.
"European Application Serial No. 06734971.2, Office Action dated Aug. 29, 2007", 1 pg.
"European Application Serial No. 06734971.2, Office Action dated Oct. 8, 2007", 2 pgs.
"International Application Serial No. PCT/US2006/005089, International Preliminary Report on patentability dated Aug. 21, 2007", 6 pgs.
"International Application Serial No. PCT/US2006/005089, International Search Report dated Nov. 17, 2006", 3 pgs.
"International Application Serial No. PCT/US2006/005089, Written Opinion dated Nov. 17, 2006", 5 pgs.
"Canadian Application Serial No. 2,598,177, Response filed Oct. 7, 2013 to Office Action dated Apr. 8, 2013", 5 pgs.
"European Application Serial No. 06734971.2, Examination Notification Art. 94(3) dated Apr. 11, 2014", 4 pgs.
"Japanese Application Serial No. 2007-556232, Amendment filed Jan. 14, 2009", 2 pgs.
"Japanese Application Serial No. 2007-556232, Office Action dated Jan. 18, 2011", 2 pgs.
"Japanese Application Serial No. 2007-556232, Office Action dated Jul. 27, 2010", 2 pgs.
"Japanese Application Serial No. 2007-556232, Response filed Apr. 18, 2011 to Office Action dated Jan. 18, 2011", 4 pgs.
"Japanese Application Serial No. 2007-556232, Response filed Oct. 24, 2010 to Office Action dated Jul. 27, 2010", 7 pgs.
"European Application Serial No. 06734971.2, Response filed Oct. 21, 2014 to Examination Notification Art. 94(3) dated Apr. 11, 2014", 7 pgs.

* cited by examiner

FIG_1

FIG._2

FULLY POROUS PROSTHETIC HIP STEM

CROSS REFERENCE TO RELATED APPLICATIONS

This application claims the benefit under Title 35, U.S.C. § 119(e) of U.S. Provisional Patent Application Ser. No. 60/654,156, entitled Fully Porous Prosthetic Hip Stem, filed Feb. 18, 2005, the disclosure of which is hereby expressly incorporated herein by reference.

BACKGROUND

1. Field of the Invention

The present invention relates to a prosthetic hip stem for implantation in the femur as a component of a prosthetic hip joint. More particularly, the present invention relates to a prosthetic hip stem having a fully porous coating and a contoured neck portion.

2. Description of the Related Art

Orthopedic implants are commonly used to replace some or all of a patient's hip joint in order to restore the use of the hip joint, or to increase the use of the hip joint, following deterioration due to aging or illness, or injury due to trauma. In a hip replacement, or hip arthroplasty procedure, a femoral component is used to replace a portion of the patient's femur, including the femoral neck and head. The femoral component is typically a hip stem, which includes a stem portion positioned within the prepared femoral canal of the patient's femur and secured via bone cement, or by a press-fit followed by bony ingrowth of the surrounding tissue into a porous coating of the stem portion. The hip stem also includes a neck portion adapted to receive a prosthetic femoral head. The femoral head is received within a prosthetic acetabular component, such as an acetabular cup received within the prepared recess of the patient's acetabulum.

One known hip stem includes a core formed of either a cobalt-chromium-molybdenum alloy or titanium, and a porous surface layer in the form of a matrix of small metallic beads or a wire mesh. Typically, the porous surface layer is sintered to the core by heating the core and the porous surface layer to a high temperature in order to cause the porous surface layer and core to fuse, melt, or bond together along their interface. U.S. Pat. Nos. 6,395,327, 6,514,288, and 6,685,987, each assigned to the assignee of the present invention and hereby incorporated by reference, disclose various methods of enhancing the fatigue strength and the connection between the core and the porous surface layer of the foregoing types of hip stems.

SUMMARY

The present invention provides a prosthetic hip stem for use in a prosthetic hip joint. The hip stem generally includes a core having a stem portion and a neck portion, a polymer matrix layer substantially covering the stem portion of the core, and a porous metal layer substantially covering the polymer matrix layer. The polymer matrix layer connects the core and the porous metal layer, and may be injection molded therebetween. The neck portion of the hip stem has a relatively thin or slender profile which allows for an increased degree of articulating movement of the hip stem with respect to the acetabular component of a prosthetic hip joint. The neck portion of the hip stem additionally includes a version indicator element, such as a bump or a protrusion, which may be tactilely felt by a surgeon to aid the surgeon in positioning the hip stem during a minimally invasive total hip arthroplasty procedure, for example, where direct visualization of the hip stem by the surgeon may not be possible. Additionally, the core of the hip stem includes grooves, ridges, flats, dimples or other features to enhance the mechanical interconnection between the core and the polymer matrix layer.

In one form thereof, the present invention provides a prosthetic hip stem for implantation into bone including a core including a stem portion and a neck portion, the core including at least one of a recess feature and a protrusion feature; a polymer matrix layer substantially covering the stem portion, the polymer matrix layer cooperatively engaging the at least one of a recess feature and a protrusion feature; and a porous metal layer substantially covering the polymer matrix layer.

In another form thereof, the present invention provides a prosthetic hip stem for implantation into bone including a core including a stem portion and a neck portion, the neck portion terminating in a tapered femoral head fitting having a maximum diameter, wherein a substantial portion of the neck portion is contoured to have a lesser diameter than the maximum diameter of the femoral head fitting; and a porous metal layer substantially covering the core.

In a further form thereof, the present invention provides a prosthetic hip stem for implantation into bone including a stem portion; a neck portion extending from the stem portion and having a lateral side and a medial side, the medial side including a version indicator element.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention, in one form, and such exemplification is not to be construed as limiting the scope of the invention in any manner.

DETAILED DESCRIPTION

Figure 1:
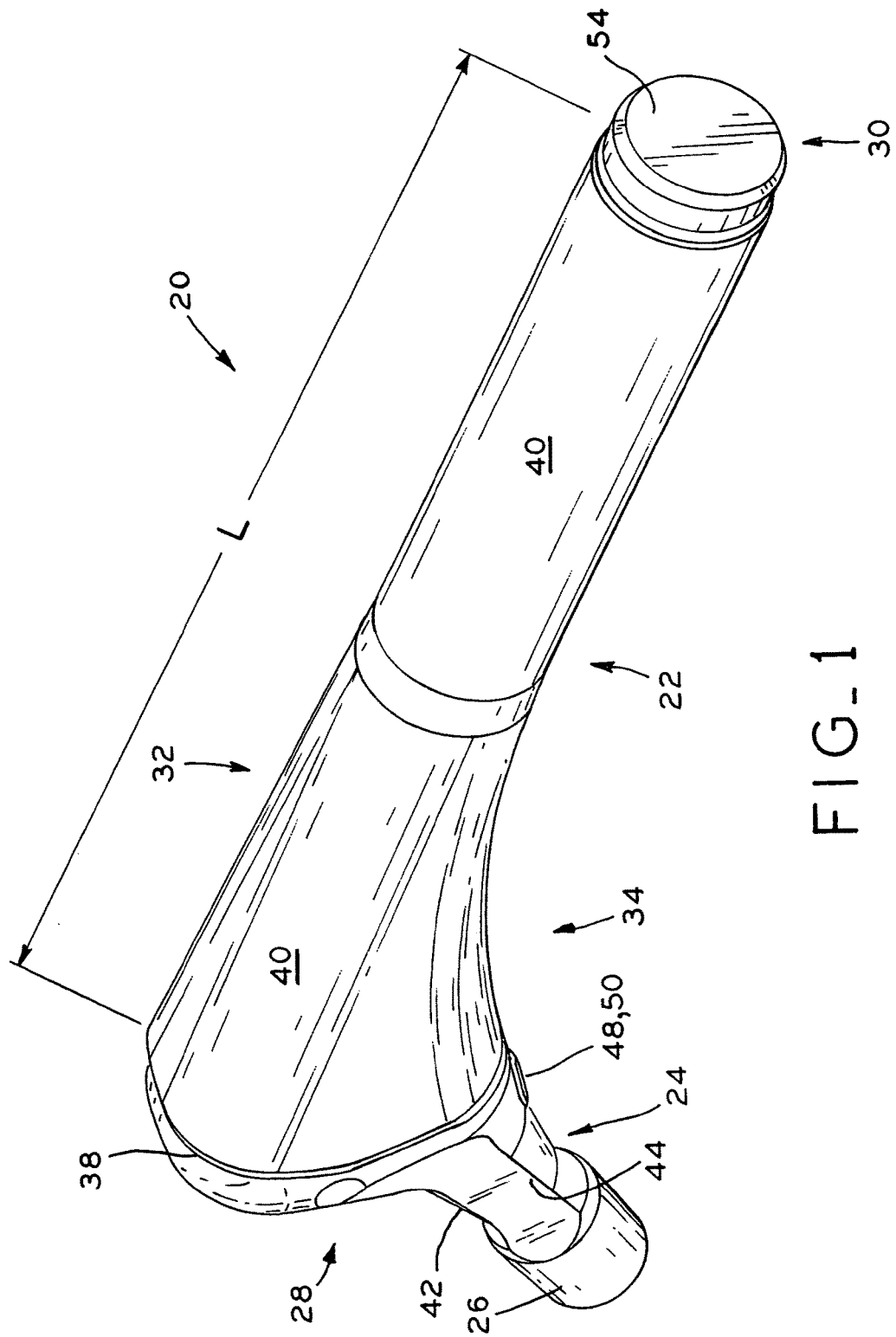
FIG. 1 is a first isometric view of a hip stem according to the present invention.

Referring to FIGS. 1-5, a prosthetic hip stem 20 according to the present invention is shown, which generally includes stem portion 22, and neck portion 24 extending at a generally obtuse angle from stem portion 22 and including a tapered femoral head fitting 26. Stem portion 22 of hip stem 20 is received within a prepared femoral canal of a patient's femur to anchor hip stem 20 within the patient's femur. As discussed below, a femoral head component is fitted on femoral head fitting 26, and is in turn received within a prosthetic acetabular component, such as an acetabular cup seated within a prepared recess in the patient's acetabulum, to thereby provide an articulating, prosthetic hip joint. Hip stem 20 further defines proximal end 28, distal end 30, lateral side 32, medial side 34, as well as opposing anterior and posterior sides depending upon whether hip stem 20 is used with a patient's right or left femur.

Figure 3:
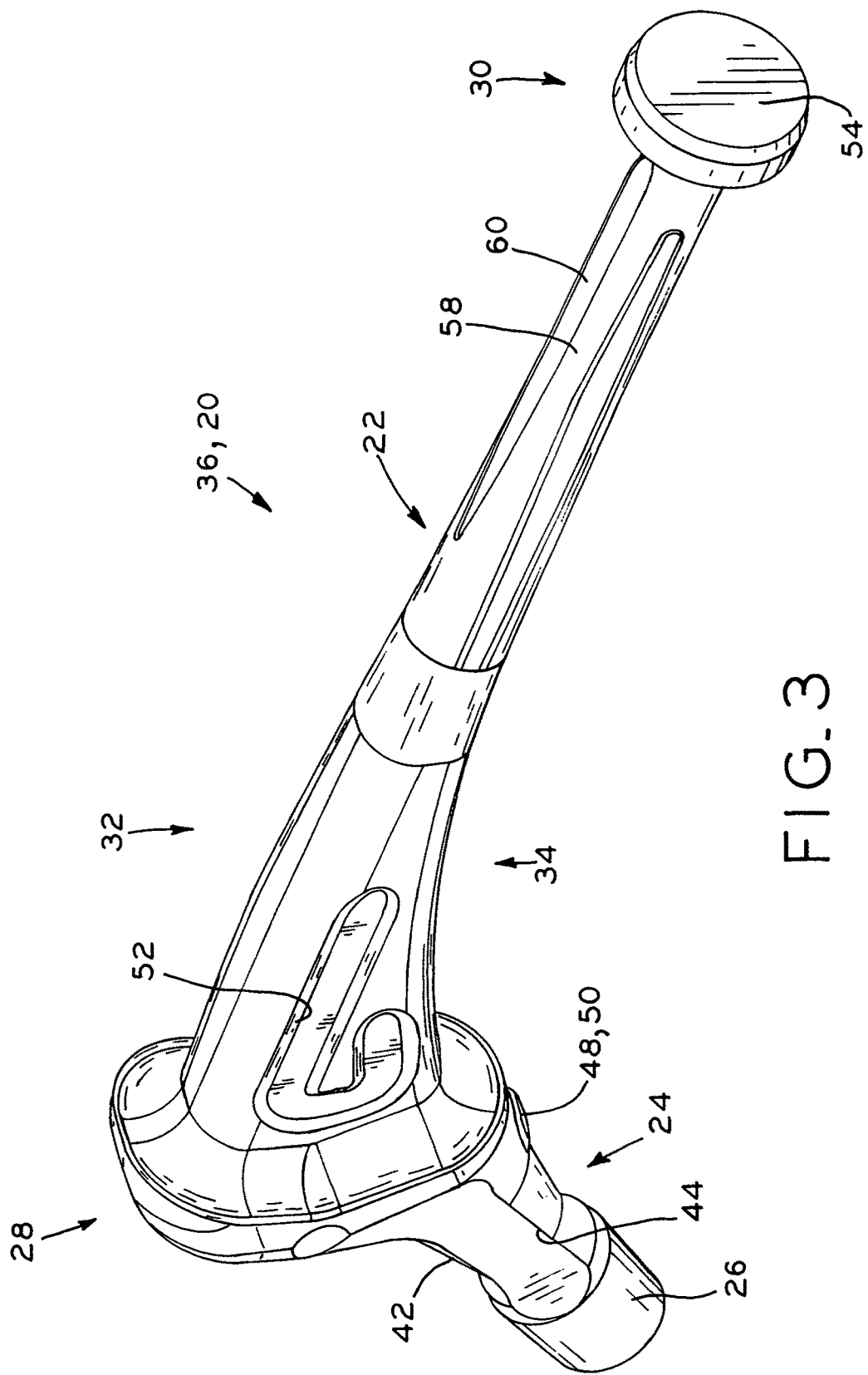
FIG. 3 is a first isometric view of the core of the hip stem of FIGS. 1 and 2.
Figure 4:
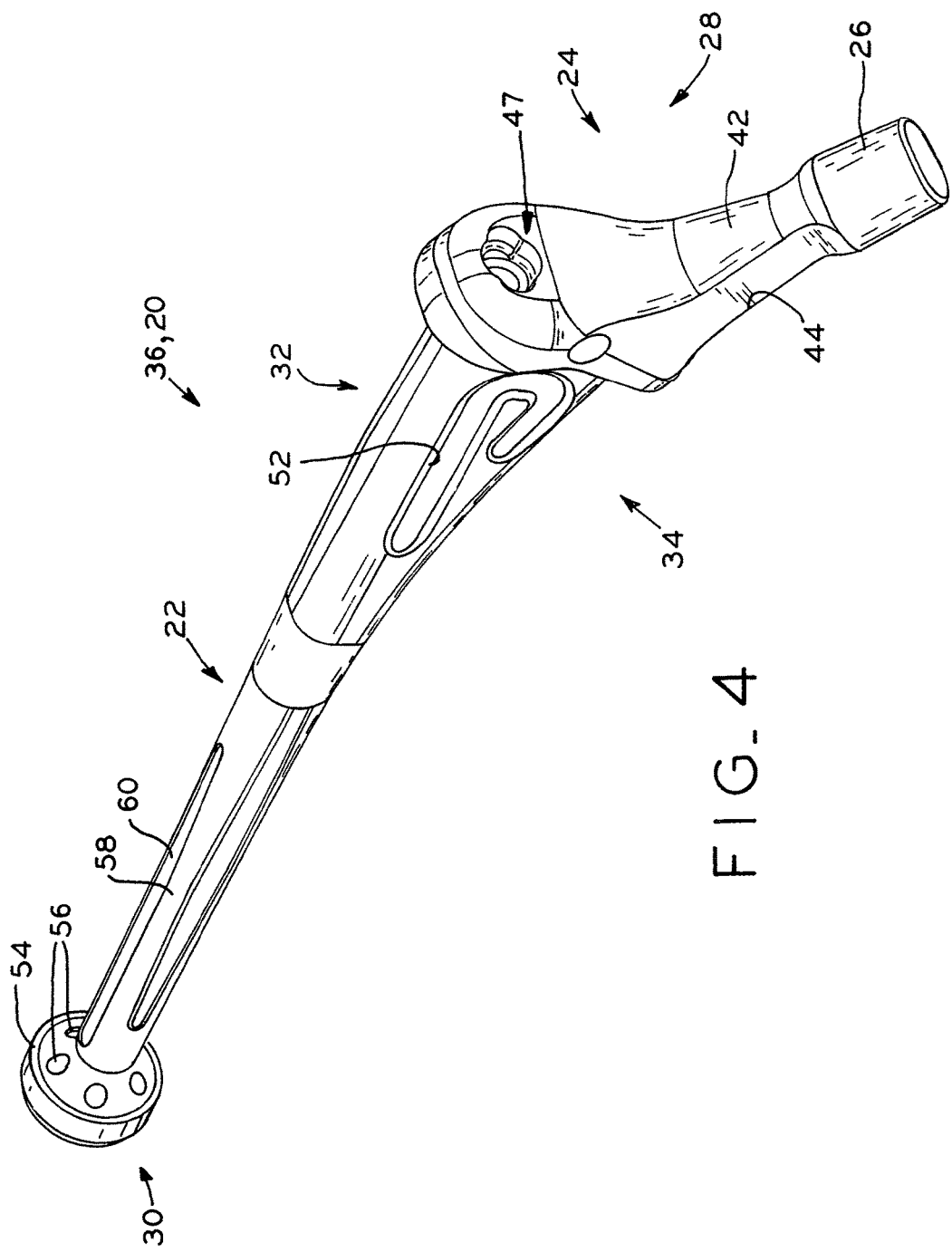
FIG. 4 is a second isometric view of the core of the hip stem of FIGS. 1 and 2.
Figure 5:
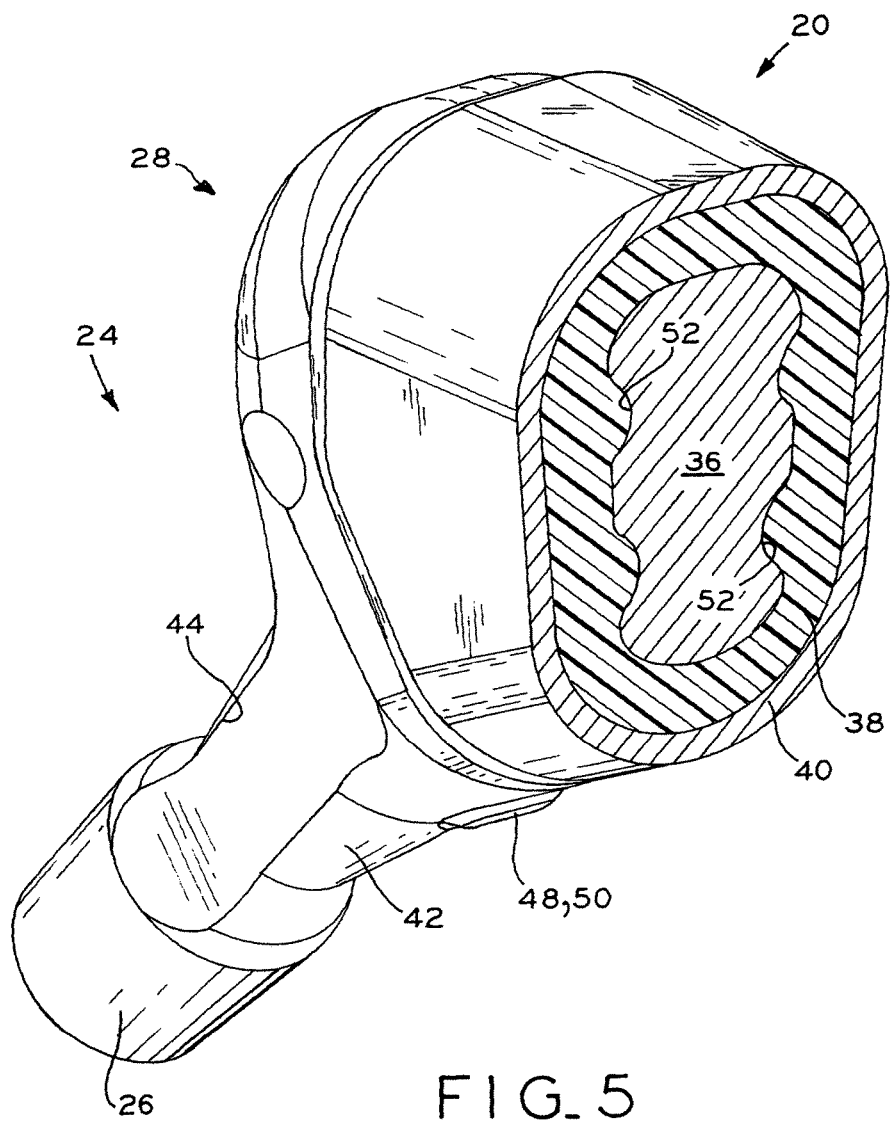
FIG. 5 is a sectional view through the hip stem, taken along line 5-5 of FIG. 2.

Referring particularly to FIGS. 3-5, hip stem 20 generally includes a substrate or core 36 generally defining stem portion 22 and neck portion 24 and, as best seen in FIG. 5, a polymer matrix layer 38 substantially covering stem portion 22 of core 36, and a porous metal layer 40 substantially covering polymer matrix layer 38. Polymer matrix layer 38 and porous metal layer 40 may cover substantially all of stem portion 22 of core 36, or alternatively, may cover only selected portions thereof, as desired. In one embodiment, stem portion 22 has a length L (FIG. 1) extending generally from proximal end 28 to distal end 30, and, in one embodiment, stops slightly short of each end 28, 30 by approximately 0.3 inches. Porous metal layer 40 extends along length L from approximately 10, 20, 30% thereof or as much as 70, 80, 90, or 95% thereof. In one embodiment, porous metal layer 40 extends along stem portion 22 for approximately 33% of the length thereof. In another embodiment, porous metal layer 40 covers approximately 33% of proximal end 28 of stem portion 22, i.e., a midcoat porous stem.

Core 36 may be made from a cobalt-chromium-molybdenum alloy or a titanium alloy, for example, via a forging or casting process, followed by machining to achieve a desired shape or profile. Polymer matrix layer 38 may be formed of an inert polyaryletherketone ("PAEK") polymer such as, for example, polyetheretherketone ("PEEK"). Porous metal layer 40 may be a metal wire mesh of titanium fibers, or alternatively, may also comprise a metal bead matrix or other porous metal structures produced in accordance with Trabecular Metal™ technology of Zimmer, Inc. of Warsaw, Ind., for example.

Hip stem 20 may be manufactured as follows. First, core 36 is forged, followed by machining core 36 after forging to form a desired shape or profile for core 36. Core 36 is then grit blasted to sufficiently roughen its surface, and then is heat treated to facilitate polymer flow across core 36 during the injection molding process. Thereafter, core 36 is positioned within an injection molding machine with stem portion 22 of core 36 positioned within porous metal layer 40, with a gap provided therebetween. Thereafter, polymer matrix layer 38 is injected into the space between core 36 and porous metal layer 40 through suitable gates, with polymer matrix layer 38 permeating into porous metal layer 40 and into the surface of stem portion 22 of core 36 via grooves 52, dimples 56, ridges 58, and/or flats 60. Upon cooling of polymer matrix layer 38, porous metal layer 40 is firmly bonded or secured to stem portion 22 of core 36. Advantageously, core 36 is not subjected to a sintering process to apply porous metal layer 40, thereby maintaining the fatigue strength of core 36.

Figure 2:
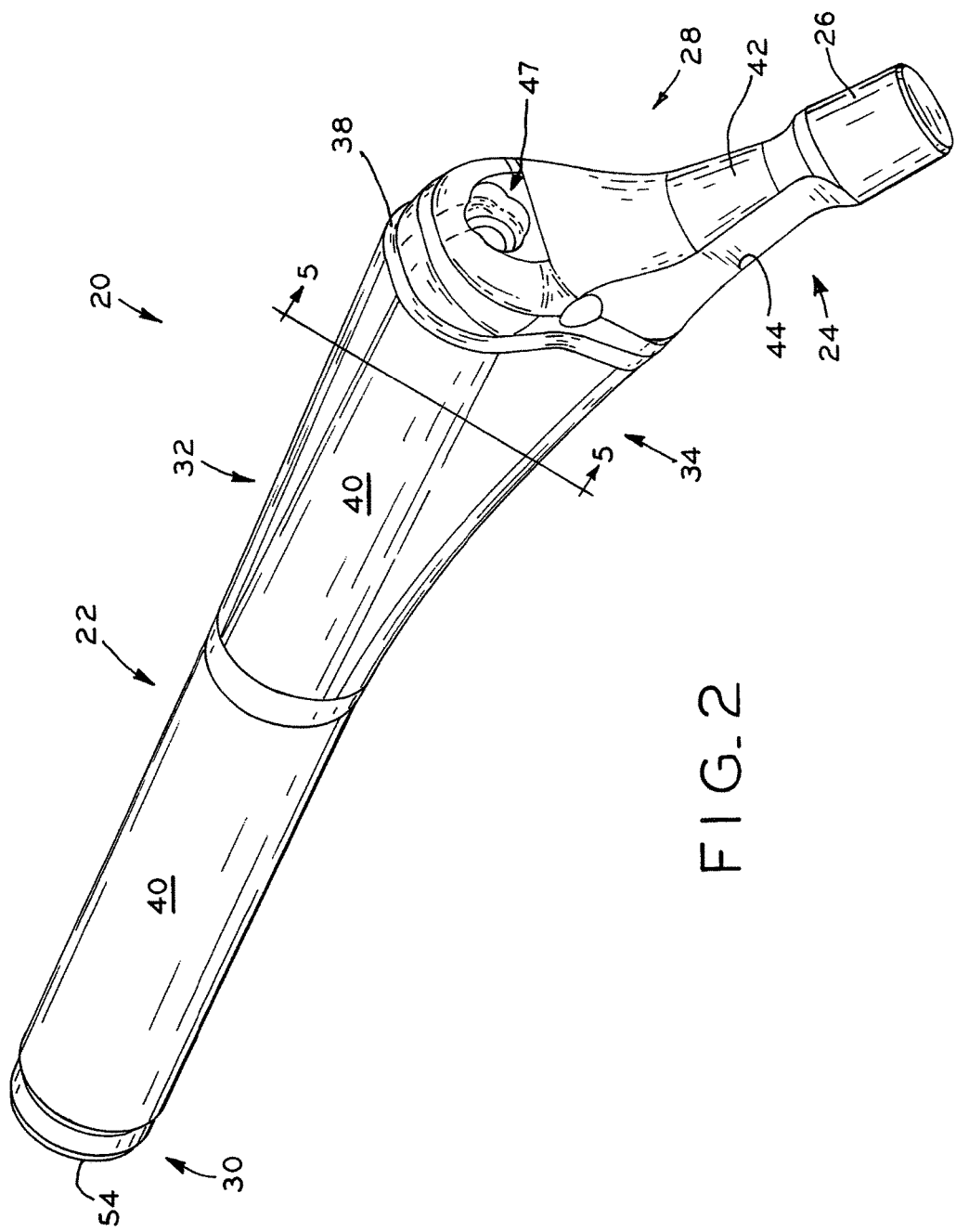
FIG. 2 is a second isometric view of the hip stem of FIG. 1.
Figure 6:
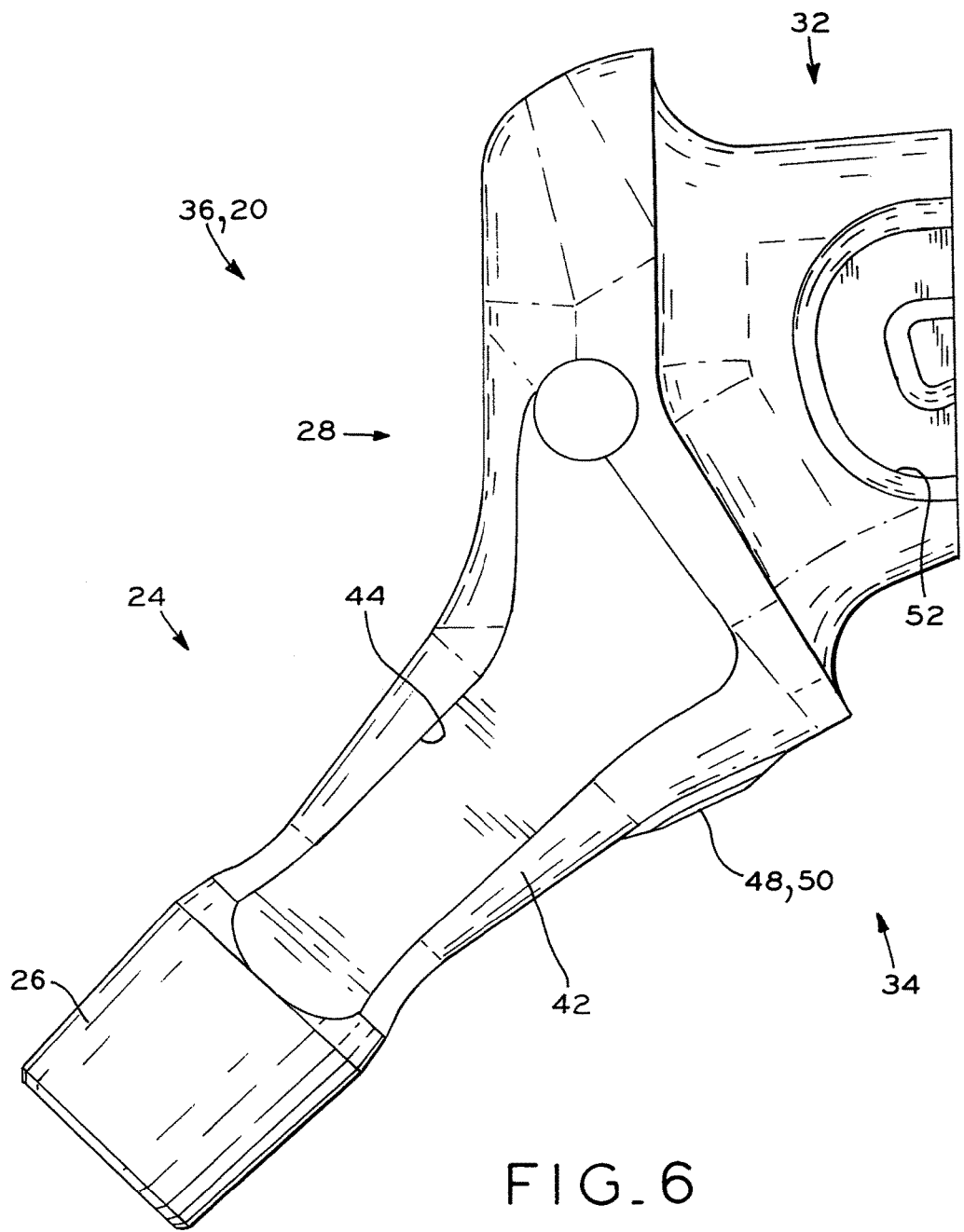
FIG. 6 is a side view of the proximal end of the hip stem, showing the contoured neck portion and the version indicator feature.
Figure 7:
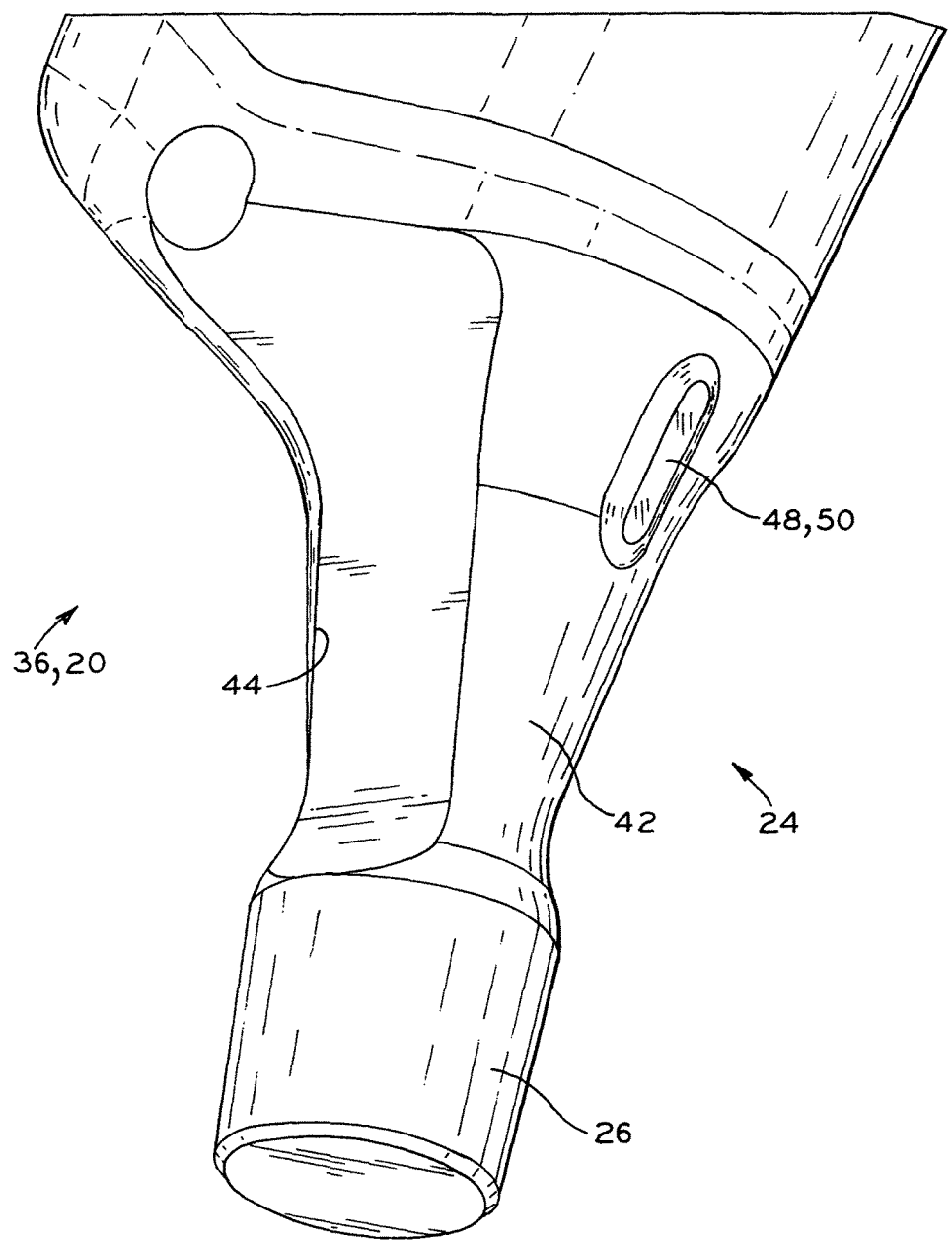
FIG. 7 is an isometric view of the proximal end of the hip stem, showing the contoured neck portion.
Figure 8:
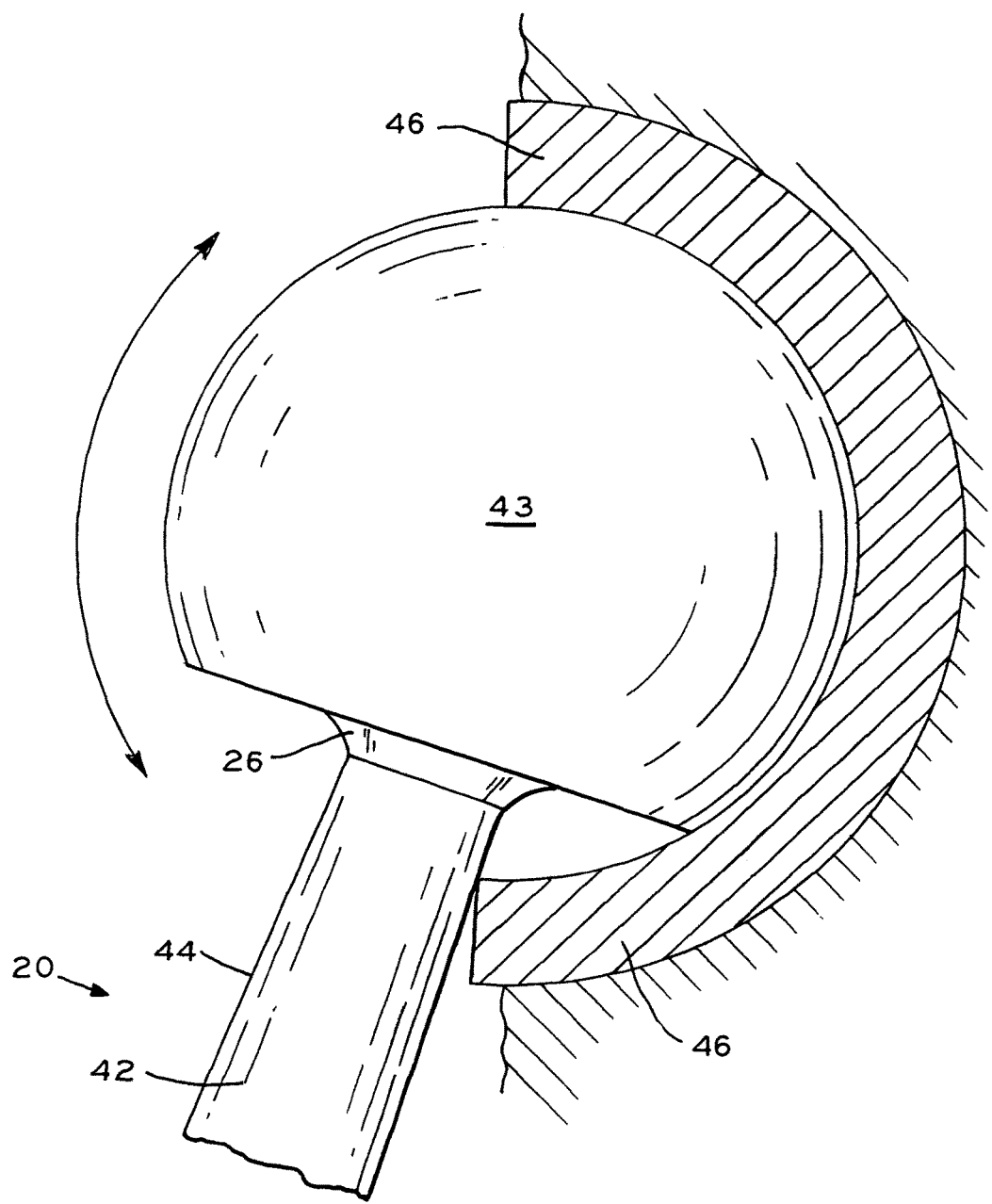
FIG. 8 is a side view of the proximal end of the hip stem, shown with a femoral head thereof fitted within an acetabular cup which is in turn positioned within an acetabulum, and illustrating the relatively large degree of articulating movement possible therebetween.

Referring to FIGS. 6-8, neck portion 24 of hip stem 20 is contoured to allow for increased articulating movement of hip stem 20 with respect to an acetabular component in a prosthetic hip joint, as illustrated in FIG. 8. As shown in FIGS. 6 and 7, neck portion 24 of hip stem 20 includes a neck section 42 which extends between stem portion 22 and femoral head fitting 26. Neck section 42 is shaped with a relatively thin or slender profile, having a diameter along a substantial portion thereof which is less than the maximum diameter of femoral head fitting 26. In particular, neck section 42 may include a plurality of scalloped recesses 44 therearound which may be formed by removal of material from the original forging of core 36 by machining. As shown in FIG. 8, the thin or slender profile of neck section 42 allows for an increased degree of angular, articulating movement of hip stem 20 with respect to the acetabular component in a prosthetic hip joint when a prosthetic femoral head 43 is fitted on fitting 26 of stem 20 and received within the acetabular component, which is shown in FIG. 8 as an acetabular cup 46 positioned within a prepared recess in the surrounding acetabulum. Also, as shown in FIGS. 2 and 4, neck portion 24 of core 36 of hip stem 20 may include an instrument engagement fitting 47 in proximal end 28 thereof within which an instrument (not shown) may be engaged to aid in driving hip stem 20 into the prepared femoral canal of a patient's femur.

Referring to FIGS. 6 and 7, neck portion 24 of hip stem 20 also includes a version indicator feature 48, which is shown herein as a bump or protrusion 50 projecting from medial side 34 of neck portion 24 of hip stem 20. As explained below, version indicator feature 48 is a tactile feature on hip stem 20 which may be felt by a surgeon during implantation of hip stem 20 to aid the surgeon in positioning hip stem 20 according to a desired version or alignment. U.S. Pat. No. 6,676,706, assigned to the assignee of the present invention and incorporated herein by reference, discloses a method for performing a "non-open", or minimally invasive, total hip arthroplasty. In the foregoing method, a small anterior incision is made for preparing a recess or seat in the acetabulum for receiving an acetabular cup, which is inserted and positioned within the acetabulum through the anterior incision. A small posterior incision is also made for preparing the femur and for receiving a hip stem, such as hip stem 20, which is positioned within the prepared femoral canal of the femur. During this and other minimally invasive procedures, the insertion of the hip stem into the prepared femoral canal may not be directly viewable by the surgeon, or may be only partially viewable by the surgeon, such as through the anterior incision.

Figure 9:
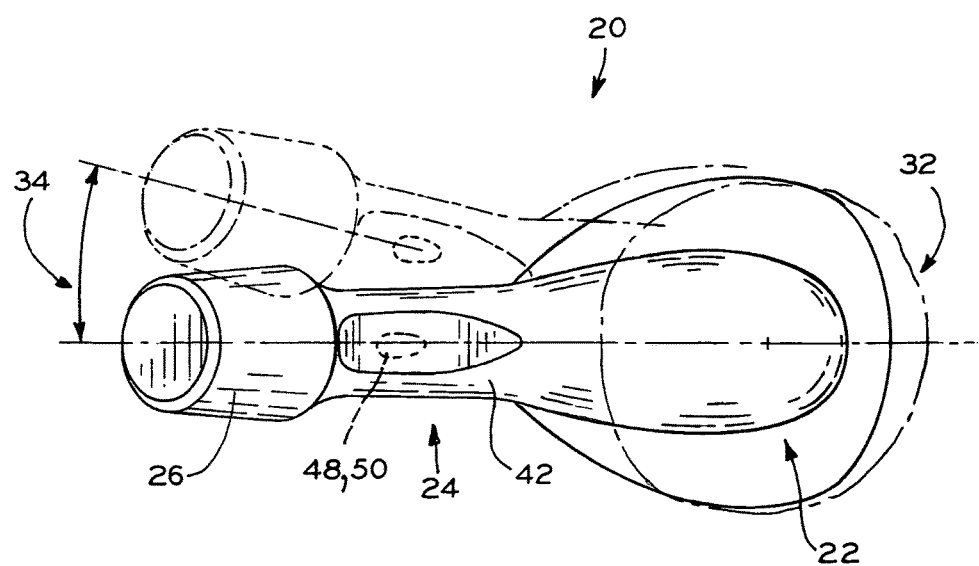
FIG. 9 is a schematic top view of the hip stem, showing relative neutral and anteversion positions of the hip stem with respect to a patient in solid and dashed lines, respectively.

Referring to FIG. 9, upon insertion of hip stem 20 into the prepared femoral canal through a posterior incision, a surgeon may feel protrusion 50 of version indicator element 48 by inserting the surgeon's fingers through the anterior incision, for example, to position hip stem 20 in an anteversion alignment, shown in dashed lines in FIG. 9, in which neck portion 24 of hip stem 20 is rotated approximately 12° to 14° anteriorly with respect to stem portion 22 from the neutral version, or direct medial-lateral, alignment shown in solid lines in FIG. 9. Optionally, according to some surgical procedures, the surgeon may tactilely align protrusion 50 of version indicator element 48 with respect to one or more grooves which are cut in the medial calcar of the prepared femur in order to position hip stem 20. Protrusion 50 of version indicator element 48 may also be used by the surgeon to position hip stem 20 in a position other than in an anteversion alignment if needed. Thus, protrusion 50 of version indicator element 48 advantageously allows the surgeon to position hip stem 20 according to a desired alignment during a minimally invasive hip arthroplasty procedure without direct visualization of hip stem 20.

Although version indicator feature 48 is shown herein as bump or protrusion 50, other tactile elements may be used, such as a recess, a group of recesses, or a ridge or a group of ridges, for example, in medial side 34 of neck portion 24 of hip stem 20, or at another location or locations on neck portion 24 of hip stem 20.

Figure 10:
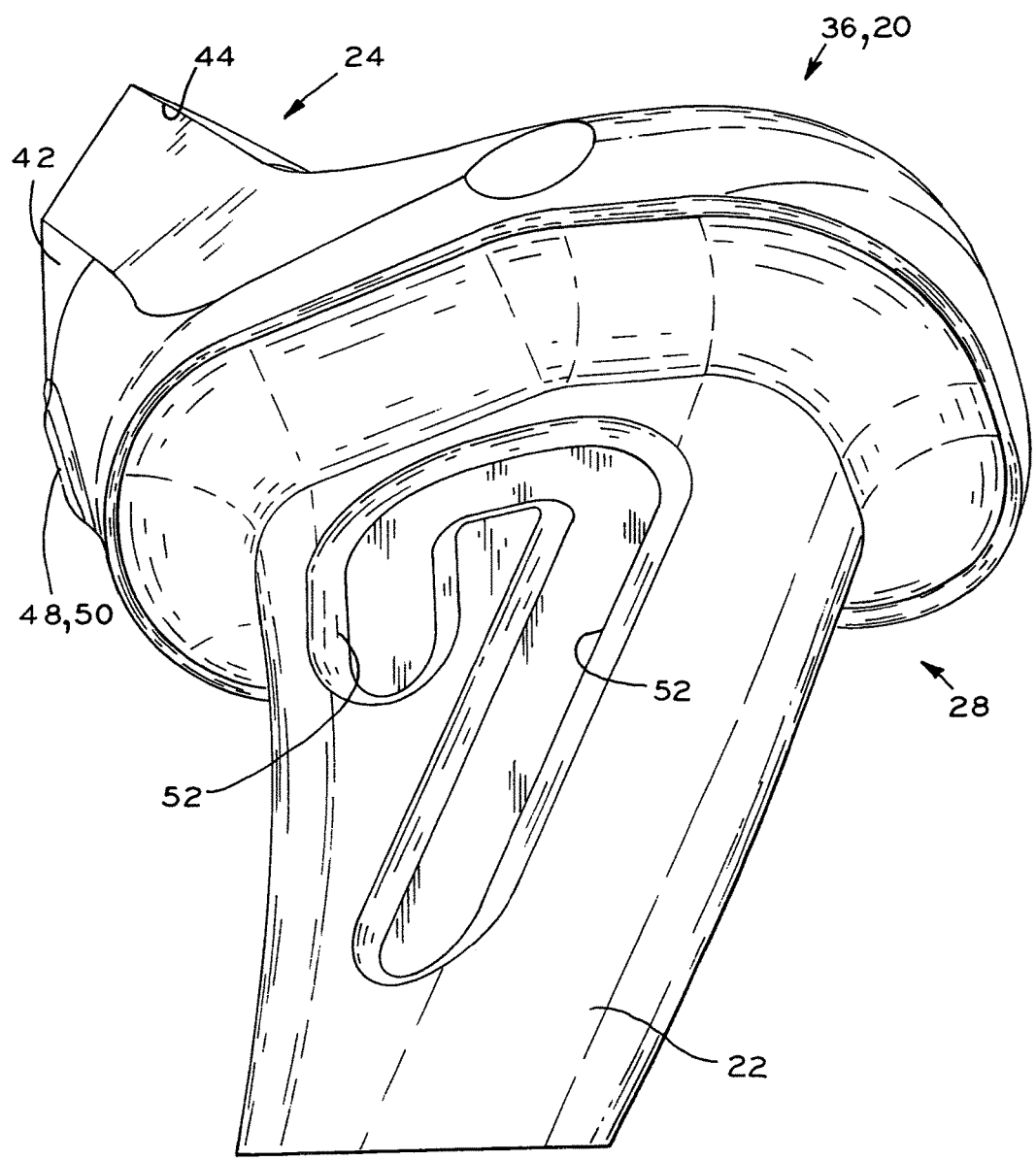
FIG. 10 is an isometric view of the proximal end of the core of the hip stem, showing the curved groove therein.
Figure 11:
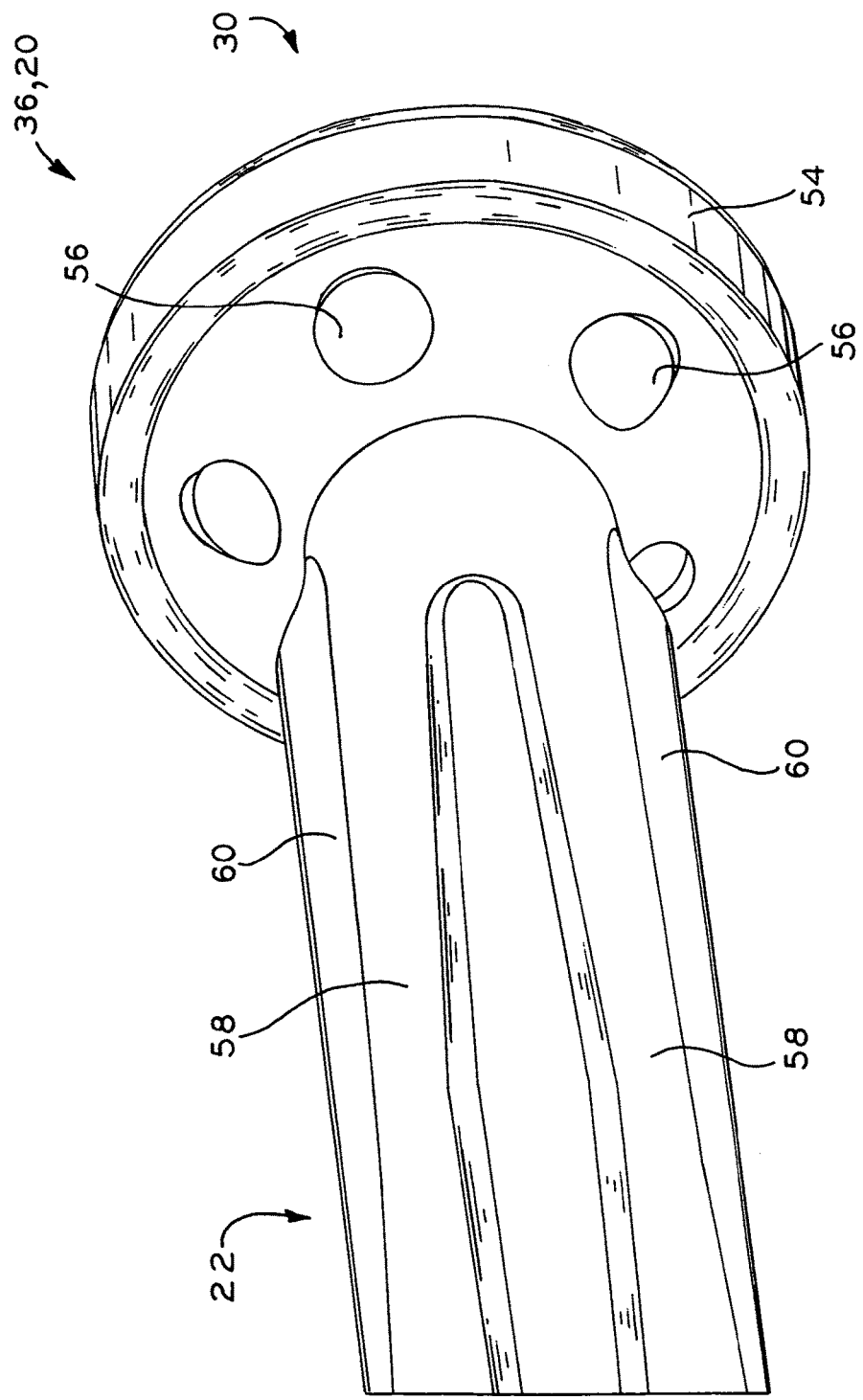
FIG. 11 is an isometric view of a portion of the distal end of the core of the hip stem, showing the distal boss of the core, including a plurality of dimples around the boss and a plurality of ridges in the stem portion of the core.

Referring to FIGS. 10 and 11, core 36 includes a plurality of features for enhancing the mechanical interconnection between core 36 and polymer matrix layer 38. As shown in FIG. 10, proximal end 28 of stem portion 22 of core 36 includes a curved, generally "candy cane"-shaped or "number 7"-shaped groove 52 on one or both of the anterior and posterior sides thereof. During manufacture of hip stem 20, in which the material of polymer matrix layer 38 is injected into the space between core 36 and porous metal layer 40, the material of polymer matrix layer 38 flows into and substantially fills grooves 52 to form a robust mechanical interconnection between core 36 and polymer matrix layer 38 upon curing of the material. The mechanical interconnection resists relative movement between core 36 and polymer matrix layer 38, such as rotational movement, responsive to torsional and/or other types of loading which may be imposed upon core 36 when hip stem 20 is used in a hip joint, and in particular, after porous metal layer 40 becomes substantially fused to the surrounding femoral bone tissue.

Referring to FIG. 11, distal end 30 of core 36 includes a boss 54 which provides a rigid leading surface for insertion of hip stem 20 into a prepared femoral canal. Boss 54 also includes a plurality of dimples 56 formed circumferentially thereabound. During manufacture of hip stem 20, in which the material of polymer matrix layer 38 is injected into the space between core 36 and porous metal layer 40, the material of polymer matrix layer 38 flows into and substantially fills dimples 56 to form a robust mechanical interconnection between core 36 and polymer matrix layer 38 upon curing of the material. The mechanical interconnection also resists relative movement, such as relative rotational movement, between core 36 and polymer matrix layer 38 responsive to torsional and/or other types of loading upon core 36 after hip stem 20 is implanted.

Still referring to FIG. 11, stem portion 22 of core 36 may additionally include further features to enhance the mechanical interconnection between core 36 and polymer matrix layer 38, such as ridges 58 and/or flats 60, or other projecting or recessed features in core 36 such as grooves, cavities, bores, dimples, bumps, protuberances, protrusions, or other features which may be formed in core 36 by forging or post-forging machining, for example. Ridges 58 and flats 60 extend longitudinally along core 36 and resist relative movement, such as relative rotational movement, between core 36 and polymer matrix layer 38 responsive to torsional and/or other types of loading which may be imposed upon core 36 as described above.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A prosthetic hip stem for implantation into bone, the prosthetic hip stem having a proximal end, a distal end, and a longitudinal axis that extends from the proximal end to the distal end, a central plane extending through the prosthetic hip stem approximately midway between the proximal end and the distal end to divide the prosthetic hip stem into a proximal region and a distal region, the prosthetic hip stem comprising:
   a core including a stem portion, a neck portion, and a boss that projects radially outwardly from said stem portion in a direction perpendicular to the longitudinal axis, said boss defining the distal end of the prosthetic hip stem, wherein the distal end of the prosthetic hip stem widens radially outwardly from said stem portion in a direction perpendicular to the longitudinal axis, said core including a proximal fixation feature located in the proximal region of the prosthetic hip stem and a distal fixation feature located in the distal region of the prosthetic hip stem, each of the proximal and distal fixation features including at least one of a recess feature and a protrusion feature, wherein said boss defines a plurality of dimples formed circumferentially therearound;
   a polymer matrix layer substantially covering said stem portion, said polymer matrix layer cooperatively engaging said proximal and distal fixation features; and
   a porous metal layer substantially covering said polymer matrix layer.

2. The prosthetic hip stem of claim 1, wherein said recess feature comprises at least one element selected from the group consisting of a groove, a flat, a cavity, a bore, and a dimple.

3. The prosthetic hip stem of claim 1, wherein said protrusion feature comprises at least one element selected from the group consisting of a ridge, a bump, and a protuberance.

4. The prosthetic hip stem of claim 1, wherein said neck portion includes a lateral side and a medial side, said medial side including a version indicator element.

5. The prosthetic hip stem of claim 1, further comprising an instrument engagement structure disposed in the proximal end of the prosthetic hip stem.

6. The prosthetic hip stem of claim 1, wherein said neck portion includes at least one recess.

7. The prosthetic hip stem of claim 1, wherein said neck portion terminates in a tapered femoral head fitting having a maximum diameter, wherein a substantial portion of said neck portion is contoured to have a lesser diameter than said maximum diameter of said femoral head fitting.

8. The prosthetic hip stem of claim 4, wherein said version indicator element comprises a projection on said medial side of said neck portion.

9. The prosthetic hip stem of claim 1, wherein said proximal fixation feature includes an anterior and/or posterior groove in said core.

10. A prosthetic hip stem for implantation into bone comprising:
a core including:
a stem portion having a distal end and a proximal end, a central plane extending through said stem portion approximately midway between said proximal end and said distal end to divide said stem portion into a proximal region and a distal region;
a neck portion extending from said proximal end of said stem portion, the prosthetic hip stem narrowing from said neck portion to said stem portion;
a boss projecting radially outwardly from said distal end of said stem portion, the prosthetic hip stem narrowing from said boss to said stem portion, said neck portion and said boss cooperating to define a cavity along said stem portion between said neck portion and said boss, wherein said boss includes a distal surface that defines a distal end of the prosthetic hip stem and a proximal surface that faces said cavity to support said polymer matrix layer in said cavity between said neck portion and said boss, with a plurality of dimples being formed in said proximal surface of said boss;
a proximal fixation feature located in said proximal region of said stem portion; and
a distal fixation feature located in said distal region of said stem portion, each of said proximal and distal fixation features including at least one of a recess feature and a protrusion feature;
a polymer matrix layer positioned in said cavity between said neck portion and said boss and substantially covering said stem portion, said polymer matrix layer cooperatively engaging said proximal and distal fixation features; and
a porous metal layer substantially covering said polymer matrix layer.

11. The prosthetic hip stem of claim 10, wherein said proximal fixation feature includes an anterior and/or posterior groove in the proximal region of the stem portion.

12. The prosthetic hip stem of claim 11, wherein said anterior and/or posterior groove is candy cane-shaped or number 7-shaped.

13. The prosthetic hip stem of claim 1, wherein said proximal fixation feature differs in shape from said distal fixation feature.

14. The prosthetic hip stem of claim 1, wherein said proximal fixation feature includes a J-shaped recess.

15. The prosthetic hip stem of claim 1, wherein said distal fixation feature includes a plurality of elongate, longitudinal recesses.

16. The prosthetic hip stem of claim 1, wherein said polymer matrix layer is located between said porous metal layer and said plurality of dimples in said boss, said polymer matrix layer cooperatively engaging said plurality of dimples in said boss to attach said porous metal layer to said boss.

17. The prosthetic hip stem of claim 10, wherein said proximal fixation feature differs in shape from said distal fixation feature.

18. The prosthetic hip stem of claim 10, wherein said proximal fixation feature includes a J-shaped recess.

19. The prosthetic hip stem of claim 10, wherein said distal fixation feature includes a plurality of elongate, longitudinal recesses.

20. The prosthetic hip stem of claim 10, wherein said polymer matrix layer is located between said porous metal layer and said plurality of dimples in said boss, said polymer matrix layer cooperatively engaging said plurality of dimples in said boss to attach said porous metal layer to said boss.

21. A prosthetic hip stem for implantation into bone, the prosthetic hip stem having a proximal end, a distal end, and a longitudinal axis that extends from the proximal end to the distal end, the prosthetic hip stem comprising:
a core including a stem portion, a neck portion, and a boss, wherein the boss defines the distal end of the prosthetic hip stem and projects radially outwardly from said stem portion in a direction perpendicular to said longitudinal axis, said boss including a proximal surface with a plurality of dimples being formed in said proximal surface, said core including at least one of a recess feature and a protrusion feature;
a polymer matrix layer substantially covering said stem portion, said polymer matrix layer cooperatively engaging said at least one of a recess feature and a protrusion feature; and
a porous metal layer substantially covering said polymer matrix layer.

22. The prosthetic hip stem of claim 21 having a central plane extending through the prosthetic hip stem approximately midway between the proximal end and the distal end to divide the prosthetic hip stem into a proximal region and a distal region, with a proximal fixation feature located in the proximal region of the prosthetic hip stem and a distal fixation feature located in the distal region of the prosthetic hip stem, each of the proximal and distal fixation features including at least one of a recess feature and a protrusion feature.

23. The prosthetic hip stem of claim 21, wherein said neck portion and said boss cooperate to define a cavity along said stem portion between said neck portion and said boss, wherein the proximal surface of said boss facing said cavity to support said polymer matrix layer.

24. The prosthetic hip stem of claim 23, wherein said polymer matrix layer is received in said plurality of dimples for attaching said polymer matrix layer to said core.

* * * * *